US00PP33542P2

(12) United States Plant Patent
Carruth

(10) Patent No.: US PP33,542 P2
(45) Date of Patent: Oct. 12, 2021

(54) HYBRID TEA ROSE PLANT NAMED 'WEKNEWIBPUSBI'

(50) Latin Name: *Rosa hybrida*
Varietal Denomination: WEKnewibpusbi

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 16/949,987

(22) Filed: Nov. 23, 2020

(51) Int. Cl.
*A01H 5/02* (2018.01)
*A01H 6/74* (2018.01)

(52) U.S. Cl.
USPC ..... Plt./130

(58) Field of Classification Search
USPC ..... Plt./132, 130, 137–140
CPC ... A01H 5/02; A01H 5/00; A01H 6/74; A01H 6/749
See application file for complete search history.

(56) References Cited

U.S. PATENT DOCUMENTS

PP6,262 P * 8/1988 Stephens ..... Plt./140
PP11,014 P 7/1999 Dorieux
PP16,614 P3 6/2006 Carruth

OTHER PUBLICATIONS

Edmunds' Roses Perfume factory Hybrid Tea Rose, retrieved on Mar. 29, 2021, retrieved from the Internet at https://www.edmundsroses.com/product/E24094/13, 4 pp. (Year: 2021).*
Great Milwaukee Rose Society, Rose Scents 2020, retrieved on Mar. 29, 2021, retrieved from the Internet at https://ncdrose.org/sites/default/files/Rose%20Scents%20January%202020%20no%20pg%2010.pdf, 10 pp. (Year: 2020).*
"Big Purple Hybrid Tea Rose", www.edmundsroses.com/product/E23548/13, 4 pages, accessed Jan. 27, 2021.

* cited by examiner

*Primary Examiner* — June Hwu
(74) *Attorney, Agent, or Firm* — McKee, Voorhees & Sease, PLC

(57) ABSTRACT

A new variety of Hybrid Tea rose suitable for garden decoration, having flowers of magenta coloration.

1 Drawing Sheet

Classification: The present invention relates to a new *Rosa hybrida* plant.

Variety denomination: The new plant has the varietal denomination 'WEKnewibpusbi'.

BACKGROUND OF THE INVENTION

This invention relates to a new and distinct variety of Hybrid Tea Rose. It has as its seed parent the variety known as 'WEKhilpurnil' (U.S. Plant Pat. No. 16,614) and an unnamed, non-disseminated seedling of my creation as its pollen parent with the following genetic origin Wild Blue Yonder x (seedling x 'STEbigpu' (U.S. Plant Pat. No. 6,262).

SUMMARY OF THE INVENTION

Among the features which distinguish the new variety from other presently available and commercial rose cultivars known to the inventor are the following combinations of characteristics: its elegant flowers of magenta coloration, its strong fruity fragrance with hints of spices, its excellent color stability throughout the life of the flower and its numerous hairs on the surface of the bud. The plant has a bushy upright moderately spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKnewibpusbi' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKhilpurnil' by the following combination of characteristics: whereas 'WEKnewibpusbi' bears flowers of magenta coloration with a strong fruity fragrance with hints of spices, 'WEKhilpurnil' bears flowers of lavender blushed purple coloration with a strong citrus blossom fragrance. The new variety has a bushy upright moderately spreading growing habit (about 122 to about 155 cm. spread at the widest point), whereas the seed parent has an upright significantly narrower growing habit (about 57 to about 72 cm. spread at the widest point).

The new variety may be distinguished from its pollen parent, a non-disseminated seedling of my creation by the following combination of characteristics: whereas 'WEKnewibpusbi' bears medium to large sized flowers (about 7.9 to about 12.7 cm. in diameter) of magenta coloration, the non-disseminated seedling bears significantly smaller flowers (about 6.8 to about 7.8 cm. in diameter) of purple striped lavender coloration. The new variety has a bushy upright moderately spreading medium height growing habit (about 122 to about 158 cm. in height), whereas the pollen parent has a rounded bushy significantly shorter growing habit (about 75 to about 82 cm. in height).

COMPARISON WITH THE CLOSEST COMMERCIALLY AVAILABLE CULTIVAR

The new variety may be distinguished from its closest commercially available cultivar, 'DORient' (U.S. Plant Pat. No. 11,014) by the following combination of characteristics: whereas 'WEKnewibpusbi' bears double flowers (about 39 to 50 petals) of magenta coloration, 'DORient' bears double flowers of purple coloration with significantly lesser petalage (about 25 to 30 petals). The new variety has a bushy upright moderately spreading medium height growing habit (about 122 to about 158 cm. in height), whereas the closest commercially available cultivar has an upright significantly taller growing habit (about 185 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

Flower: The new variety sometimes bears its flowers singly, sometimes in clusters of two to five per stem. Flowers may be borne in regular rounded clusters on strong medium to somewhat long stems (about 18 to about 64 cm.). The cluster ranges from about 20.5 to about 26.5 cm. in diameter. Outdoors, the plant blooms abundantly and nearly continuously during the growing season. The flowers have a strong fruity fragrance with hints of spices.

Bud: The peduncle is about 3.9 to about 7.3 cm. in length, of average caliper (about 0.2 to about 0.4 cm. in diameter), and usually erect. It is somewhat rough, with many stipitate glands, and some hairs. Peduncle color is between 146B and 146C often heavily suffused, especially on the side exposed to the sun, with between 187B and 187A. Before the calyx breaks, the bud is about 1.5 to about 1.9 cm. in diameter at the widest point, about 1.4 to about 2.1 cm. in length, and pointed to somewhat ovoid in shape. The surface of the bud bears between 8 to 12 foliaceous appendages with some stipitate glands and numerous puberulent hairs, usually with moderately stout entire foliaceous parts extending beyond the tip of the bud about ¼ or more of its length. Bud color is between 146B and 146A sometimes moderately suffused, especially on the side exposed to the sun, with between 187B and 187A. The sepals are 5 per flower, about 1.2 to about 3.9 cm. in length and about 0.6 to about 1.1 cm. in width at the widest point. The outer surface color of the sepal is between 146B and 146A sometimes moderately suffused, especially on the side exposed to the sun, with between 187B and 187A. The outer surface of the sepal is smooth and bears between 0 to 6 foliaceous appendages with some stipitate glands and numerous hairs. The inner surface color of the sepal is near 146D broadly bordered by near 137C. After the sepals open, the inner surface color is sometimes moderately suffused, especially on the area exposed to the sun, with between 187B and 187A. The inner surface of the sepal is covered with fine wooly tomentum; sepal margins are entire and lined with many numerous stipitate glands and hairs. The sepals are moderately permanent, and usually straight in shape with acute apices. The receptacle of the flower is of somewhat short length (about 0.3 to about 0.5 cm.) and moderately thin in caliper (about 0.6 to about 0.9 cm. in diameter). The receptacle is cup-shaped in form. Its surface is smooth with few hairs and with somewhat thin fleshy walls. The receptacle color is between 144A and 146C sometimes moderately suffused, especially on the side exposed to the sun, with between 187B and 187A. As the petals open (after the calyx breaks), the bud is about 1.5 to about 2.2 cm. in diameter at the widest point, about 2.0 to about 3.0 cm. in length, and pointed to somewhat ovoid in form. The color of the under surfaces of the newly opened petals is between 82D and 87D at the lower third of the petal suffusing to between 64A and 70A on the remaining surface of the petal and sometimes moderately blushed on the outermost petals with between 60A and 59B to as dark as near 187C. At the point where the petal attaches, there is a somewhat large zone of near 149D. The color of the upper surfaces of the newly opened petals is near 79D. At the point where the petal attaches, there is a moderately small zone of between 1D and 154D.

Bloom: When fully open, the bloom ranges from about 7.9 to about 12.7 cm. in diameter. Petalage is double with about 39 to 50 petals and about 10 to 19 petaloids irregularly arranged. When partially open, the bloom form is moderately ovoid to somewhat high centered to cupped, and the petals are moderately tightly spiraled to cupped with petal edges somewhat reflexed outward. When fully open, the bloom form is more cupped, and the petals are loosely cupped to somewhat undulated with petal edges moderately reflexed outward.

Petals: The substance of the petals is somewhat heavy and of moderately thin thickness, with upper surfaces moderately satiny and under surfaces somewhat shiny. The petals are about 2.8 to about 6.2 cm. in length and about 2.5 to about 5.7 cm. in width at the widest point. Petal margins are entire. The outer & inner petals are somewhat obovate in shape with rounded apices. Petaloids are about 1.1 to about 4.6 cm. in length and about 0.5 to about 3.9 cm. in width at the widest point. Petaloids are irregularly shaped moderately oblanceolate to somewhat obovate to subulate with rounded apices.

Newly opened flower: The under surface color of the outer and intermediate petals is near 85D at the lower third of the petal suffusing to between 70A and 74B on the remaining surface of the petal and sometimes moderately blushed on the outermost petals with between 60B and 59C. At the point where the petal attaches, there is a somewhat small zone of near 150D. The upper surface color of the outer and intermediate petals is near 87D at the lower third of the petal suffusing to between 72A and 74B on the remaining surface of the petal. At the point where the petal attaches, there is a somewhat large zone of between 1D and 154D. The under surface color of the inner petals is near 85D at the lower third of the petal suffusing to between 61A and 74B on the remaining surface of the petal. The upper surface color of the inner petals is near 87D at the lower third of the petal suffusing to between 61A and 74B on the remaining surface of the petal. The under and upper surface colors of the petaloids are similar in coloration to the upper and under surfaces of the inner petals. The general tonality of the newly opened flower is between 72A and 74B.

Three-day-old flower: The under surface color of the outer petals is lighter than 85D at the lower third of the petal suffusing to between 81D and 78A on the remaining surface of the petal and sometimes moderately blushed on the outermost petals with between 60B and 59C. At the point where the petal attaches, there is a somewhat small zone of near 150D. The upper surface color of the outer petals is near 85D at the lower third of the petal suffusing to between 81C and lighter than 78A on the remaining surface of the petal. At the point where the petal attaches, there is a somewhat large zone of between 1D and 154D. The under surface color of the intermediate petals is lighter than 85D at the lower third of the petal suffusing to between 78B and 78A on the remaining surface of the petal. The upper surface color of the intermediate petals is near 85D at the lower third of the petal suffusing to between 72B and 78A on the remaining surface of the petal. The under surface color of the inner petals is near 85D at the lower third of the petal suffusing to between 78B and 78A on the remaining surface of the petal. The upper surface color of the inner petals is near 85D at the lower third of the petal suffusing to between 71B and 78A on the remaining surface of the petal. The under and upper surface colors of the petaloids are similar in coloration to the upper and under surfaces of the inner petals. The general tonality of the three-day-old flower is between 72B and 78A. On the spent bloom, the petals usually drop off cleanly. In November in Wasco, Calif., blooms on the bush growing outdoors generally last about four to five days. Cut roses from plants grown outdoors and kept at normal indoor living temperatures generally last about four to five days.

Male reproductive organs: Stamens are few in number (average about 55) and are arranged regularly about the pistils; a few are mixed with petaloids and sometimes tucked in the calyx. The filaments are of medium to somewhat long length (about 0.5 to about 1.2 cm.) most with anthers. Filaments are between 4C and 3D in color. The anthers are of medium size for the class and all open approximately at the same time. Anther color when immature is near 20A on the external part and near 11D on the internal part. Anther color at maturity is near 163A on the external part and near 200A on the internal part. Pollen is somewhat sparse and between 18C and 20D in color.

Female reproductive organs: Pistils vary in number (average about 125). The styles are moderately even, somewhat short to average in length (about 0.3 to about 0.8 cm.), moderately thin in caliper, and loosely bunched. Stigma color is between 14D and 16D. Style color is between 150D and 4D often heavily suffused with between 60A and 60B. Ovaries are usually all enclosed in the calyx. The ovaries are of small size and between 158B and 158C in color. Hips have not been observed on this variety when grown in Wasco, Calif.

Foliage: The compound leaves are usually comprised of three to seven leaflets and are borne abundantly. The five-leaflet leaves are about 9.5 to about 17.2 cm. in length and about 8.6 to about 14.2 cm. in width at the widest point, moderately leathery to somewhat crisp in texture on both sides, and with a strong glossy finish on the upper side and a weak to medium glossy finish on the under side. The leaflet margin undulation is absent. The leaves have a pinnate venation pattern. The terminal leaflets are about 4.5 to about 7.5 cm. in length and about 2.6 to about 4.5 cm. in width at the widest point, shaped oval to somewhat ovate with acute apices and rounded to somewhat acute bases. Their margins are usually simply serrate. The upper surface color of the mature leaf is between 137A and 139A. The under surface color of the mature leaf is between 147B and 138B. The under and upper colors of the leaf veins on the mature leaf are similar in coloration to the upper and under surfaces colors of the mature leaf. The upper surface color of the young leaf is between 146A and 137C, sometimes heavily suffused with between 183B and 187B. The under surface color of the young leaf is between 146C and 138C, often heavily suffused with between 183B and 187B. The under and upper colors of the leaf veins on the young leaf are similar in coloration to the upper and under surfaces colors of the young leaf. The rachis is about 4.7 to about 10.1 cm. in length, about 0.1 to about 0.2 cm in width at the widest point, and rough. The upper side is deeply grooved with few hairs and some stipitate glands on the edges of the grooves. The under side of the rachis is rough with some hairs, few stipitate glands and few small prickles. The rachis color is near 146D on the under side and near 146B on the upper side, often heavily suffused on the young leaves with between 187A and 187B. The stipules are about 1.5 to about 2.1 cm. in length and moderately wide (about 0.8 to about 1.1 cm.) with long straight points that usually turn out at an angle of more than 45 degrees and sometimes recurve toward the stem. The under and upper surface color of the stipule is between 137A and 137B. The upper and under surfaces of the stipules are smooth in texture. The petiole is average in caliper and rough. The upper side is deeply grooved with few hairs and some stipitate glands on the edges of the grooves. The under side of the petiole is rough with some hairs, few stipitate glands and few small prickles. The petiole is about 0.9 to about 2.4 cm. in length and about 0.1 to about 0.2 cm in width at the widest point. The petiole color is near 146D on the under side and near 146B on the upper side, often heavily suffused on the young leaves with between 187A and 187B. The plant displays an average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, Calif. The plant's winter hardiness and drought/heat tolerance are yet to be determined.

Growth: The plant has a bushy upright moderately spreading medium height growing habit (about 122 to about 158 cm. in height and about 122 to about 155 cm. spread at the widest point), with full branching. It displays moderately vigorous growth and the canes are of medium to somewhat heavy caliper for the class (about 1.2 to about 2.8 cm. in diameter at the widest point). The color of the major stems is between 146B and 146A. The major stems are rough in texture and they bear some large prickles that are about 0.7 to about 1.1 cm. in length. The large prickles are angled slightly downward with a medium length somewhat broad oval base; prickle color is between 165C and 165B sometimes lightly suffused with between 201B and 201C. The major stem bears some small prickles of similar shape and coloration. The color of the branches is between 146C and 146A. The branches are rough in texture and they bear some large prickles which are of similar size and shape to the large prickles on the major stems; prickle color is between 152D and 153B often moderately suffused with between 187C and 187D. The branches bear some small prickles of similar shape and coloration. The color of the new shoots is between 146C and 146A often moderately suffused with between 187B and 187A. The new shoots are rough in texture and they bear some large prickles which are of similar size and shape to the large prickles on the major stems; prickle color is between 152D and 153B usually heavily suffused with between 187C and 187D to as dark as near 187B. The shoots bear some small prickles of similar shape and coloration.

I claim:

1. A new and distinct variety of Hybrid Tea rose plant designated 'WEKnewibpusbi', substantially as described and illustrated herein.

* * * * *

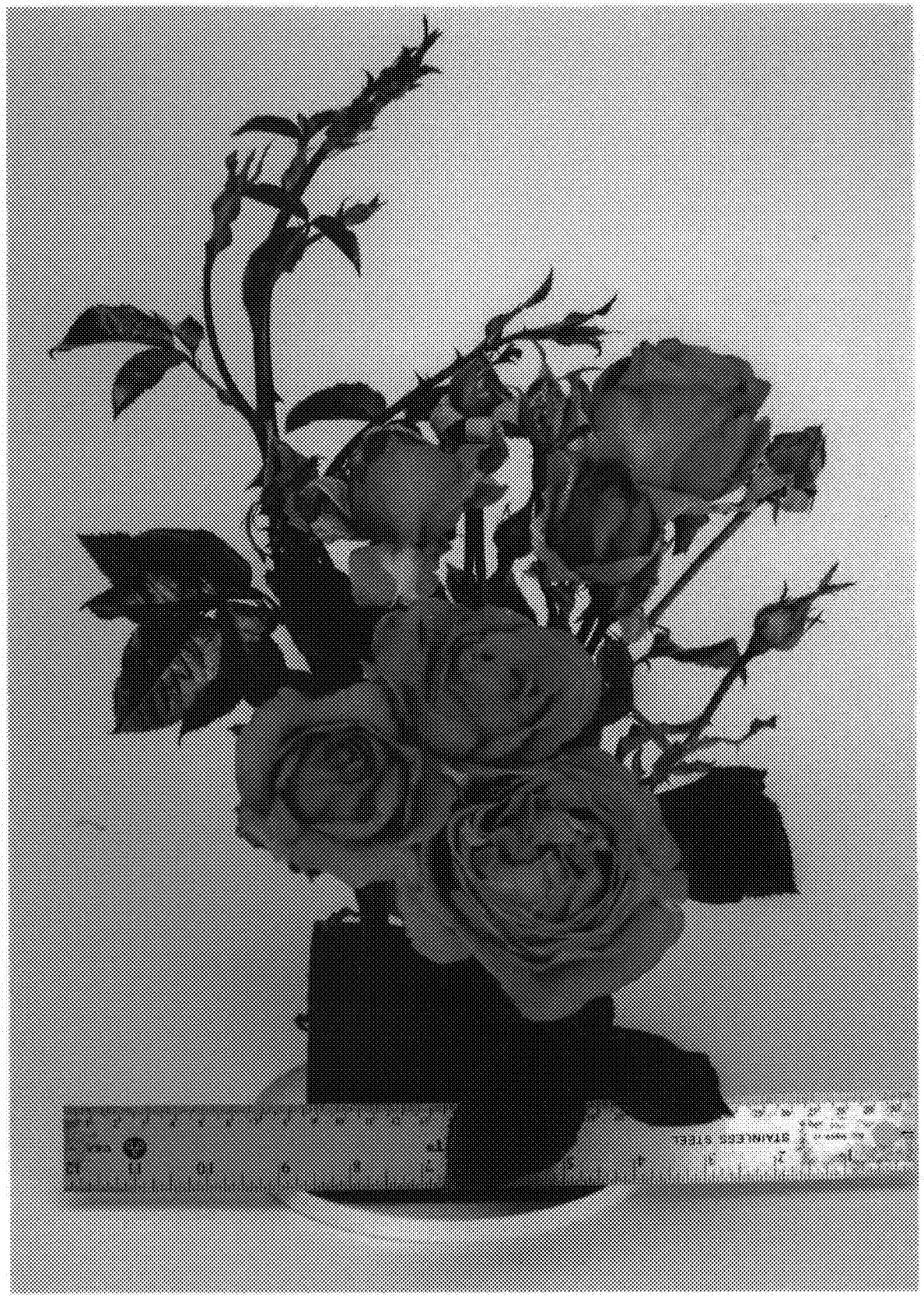
STAINLESS STEEL